US006756060B1

(12) United States Patent
Greenspan et al.

(10) Patent No.: US 6,756,060 B1
(45) Date of Patent: *Jun. 29, 2004

(54) ANTI-INFLAMMATORY AND ANTIMICROBIAL USES FOR BIOACTIVE GLASS COMPOSITIONS

(75) Inventors: David C. Greenspan, Gainesville, FL (US); Jon K. West, Gainesville, FL (US); Sean Lee, Karlsruhe (DE); James L. Meyers, Gainesville, FL (US); Mason Diamond, Gainesville, FL (US)

(73) Assignee: USBiomaterials Corp., Alachua, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/560,046

(22) Filed: Apr. 27, 2000

Related U.S. Application Data

(63) Continuation-in-part of application No. 09/164,293, filed on Oct. 1, 1998, now Pat. No. 6,428,800, which is a continuation of application No. 08/715,911, filed on Sep. 19, 1996, now Pat. No. 5,834,008, and a continuation of application No. 09/392,516, filed on Sep. 9, 1999, now abandoned.
(60) Provisional application No. 60/099,725, filed on Sep. 10, 1998.

(51) Int. Cl.$^7$ .......................... A61K 9/14; A61K 33/00; A61K 33/06; A61K 33/08; A61K 33/16
(52) U.S. Cl. ...................... 424/489; 424/400; 424/401; 424/402; 424/404; 424/405; 424/443; 424/445; 424/446; 424/447; 424/484; 424/601; 424/602; 424/606; 424/657; 424/660; 424/675; 424/688; 424/692; 424/722; 424/724; 424/DIG. 13; 514/829; 514/830; 514/831; 514/859; 514/861; 514/862; 514/863; 514/864; 514/886; 514/887; 514/951; 514/965
(58) Field of Search .................................. 424/400, 401, 424/484, 489, 601–602, 606, 657, 660, 675, 688, 692, 722, 724, 402, 404, 405, 443, 445, 446, 447, DIG. 13; 623/11.11; 514/829–831, 859, 861, 862, 863, 864, 886, 887, 951, 965; 602/41–45; 604/304, 305, 309, 310, 311, 903

(56) References Cited

U.S. PATENT DOCUMENTS

| 4,103,002 A | 7/1978 | Hench et al. ................ 428/155 |
| 4,272,518 A | 6/1981 | Moro et al. .............. 424/78.06 |
| 4,303,066 A | 12/1981 | D'Andrea ..................... 602/52 |
| 4,538,603 A | 9/1985 | Pawelchak et al. ........... 602/56 |
| 4,539,200 A | 9/1985 | Quarfoot ................. 424/78.06 |
| 4,599,209 A | 7/1986 | Dautzenberg et al. .......... 264/7 |
| 4,605,415 A | 8/1986 | Richez ....................... 424/422 |
| 4,613,502 A | 9/1986 | Turkova et al. ............ 424/94.3 |
| 4,837,285 A | 6/1989 | Berg et al. .................. 530/356 |
| 4,851,046 A | 7/1989 | Low ............................. 106/35 |
| 5,000,746 A | 3/1991 | Meiss ........................ 604/304 |
| 5,017,627 A | 5/1991 | Bonfield et al. ............ 523/115 |
| 5,068,122 A | 11/1991 | Kokubo et al. .............. 427/2.1 |
| 5,126,141 A | 6/1992 | Henry ........................ 424/423 |
| 5,263,992 A | 11/1993 | Guire ........................ 623/66.1 |
| 5,290,544 A | 3/1994 | Shimono et al. .............. 424/63 |
| 5,298,260 A | 3/1994 | Viegas et al. ............... 424/486 |
| 5,340,776 A | 8/1994 | Paschke et al. ............... 501/11 |
| 5,352,715 A | 10/1994 | Wallace ..................... 523/115 |
| 5,410,016 A | 4/1995 | Hubbell et al. ............. 528/354 |
| 5,501,706 A | 3/1996 | Arenberg ..................... 623/16 |
| 5,591,453 A | 1/1997 | Ducheyne et al. .......... 424/484 |
| 5,648,301 A | 7/1997 | Ducheyne .................... 501/39 |
| 5,681,575 A | 10/1997 | Burrell et al. .............. 424/423 |
| 5,681,872 A | 10/1997 | Erbe .......................... 523/114 |
| 5,696,169 A | 12/1997 | Otsu et al. .................. 514/675 |
| 5,702,715 A | * 12/1997 | Nikolaychik et al. ....... 424/402 |
| 5,728,753 A | 3/1998 | Bonfield et al. ............. 523/114 |
| 5,753,251 A | 5/1998 | Burrell et al. .............. 424/426 |

(List continued on next page.)

FOREIGN PATENT DOCUMENTS

| JP | 8-126659 | * 5/1996 |
| WO | 97/17401 | 3/1994 |
| WO | 98/11853 | * 3/1998 |
| WO | 99/13852 | 3/1999 |
| WO | 00/66086 | 11/2000 |

OTHER PUBLICATIONS

Medline abstract, accession No. 85209111, 1990.*
Medline abstract, accession No. 89036678, 1990.*
Derwent abstract, accession No. 1996–294740, abstractig JP 8–126659.*

(List continued on next page.)

*Primary Examiner*—John Pak
(74) *Attorney, Agent, or Firm*—Burns, Doane, Swecker & Mathis, L.L.P.

(57) ABSTRACT

Compositions and methods for treating wounds to significantly reduce the healing time, reduce the incidence of scar formation, improve the success of skin grafts, reduce the inflammatory response and providing anti-bacterial treatments to a patient in need thereof, that include small non-interlinked particles of bioactive glass or highly porous bioactive glass, are disclosed. Anti-bacterial solutions derived from bioactive glass, and methods of preparation and use thereof, are also disclosed. The compositions include non-interlinked particles of bioactive glass, alone or in combination with anti-bacterial agents and/or anti-inflammatory agents. The compositions can include an appropriate carrier for topical administration. Anti-bacterial properties can be imparted to implanted materials, such as prosthetic implants, sutures, stents, screws, plates, tubes, and the like, by incorporating small bioactive glass particles or porous bioactive glass into or onto the implanted materials. Anti-bacterial properties can also be imparted to devices used for in vitro and ex vivo cell culture by incorporating non-interlinked particles of bioactive glass into the devices. Anti-bacterial compositions derived from aqueous extracts of bioactive glass are also disclosed. These compositions can be used, for example, in food preparation, solutions used for cell culture, and buffer solutions, such as i.v. solutions.

10 Claims, No Drawings

U.S. PATENT DOCUMENTS

| | | | |
|---|---|---|---|
| 5,766,253 A | * 6/1998 | Brosnahan, III | 623/17 |
| 5,766,611 A | 6/1998 | Shimono et al. | 424/401 |
| 5,807,641 A | 9/1998 | Oku et al. | 428/701 |
| 5,834,008 A | * 11/1998 | Greenspan et al. | 424/443 |
| 5,840,290 A | 11/1998 | Hench et al. | 424/423 |
| 5,972,384 A | * 10/1999 | Thut et al. | 424/484 |
| 5,977,204 A | * 11/1999 | Boyan et al. | 523/113 |
| 5,981,412 A | * 11/1999 | Hench et al. | 501/5 |
| 5,990,380 A | 11/1999 | Marotta et al. | 623/11.11 |
| 6,083,521 A | 7/2000 | Acemoglu et al. | 424/422 |
| 6,086,374 A | 7/2000 | Litkowski et al. | 433/217.1 |
| 6,171,986 B1 | * 1/2001 | Zhong et al. | 501/12 |
| 6,338,751 B1 | * 1/2002 | Litkowski et al. | 106/35 |
| 6,428,800 B2 | * 8/2002 | Greenspan et al. | 424/405 |

OTHER PUBLICATIONS

Medline Abstract, Accession No. 85076876, 1984.*

*An Introduction to Bioceramics*, L. Hench and J. Wilson, Eds., World Scientific, New Jersey (1993).

Aydin, M., et al, "Deposition Profile of Antibacterial Anodic Silver in Root Canal Systems of Teeth", *J. Biomed. Mater. Res.*, 38(1):49–54, (John Wiley & Sons, Inc.) 1997.

Bergna, H.E., "The Colloid Chemistry of Silica", *Advances in Chemistry*, Series 234 (American Chemical Society, Washington, DC) 1994.

Bosetti, M., et al., "Effects of Bioactive Glass on Macrophages Activation", *Bioceramics*, 11: 319–322, (Word Scientific Pub. Co.) 1998.

Brinker, C. J., et al., "The Physics and Chemistry of Sol–Gel Processing", *Sol–Gel Science*, 8: 499–503 (Academic Press, Inc.) 1990.

Brinker, C. J., et al., "The Physics and Chemistry of Sol–Gel Processing,", *Sol–Gel Science*, 3: 115–119 (Academic Press, Inc.) 1990.

Carlisle, E. M., "Silicon Biochemistry, Silicon as an Essential Trace Element in Animal Nutrition", *Ciba Foundation Symposium 121*, 123–139 (John Wiley and Sons, New York) 1986.

Cartmell, S. H., et al., "Soft Tissue Response to Glycerol-suspended Controlled–release Glass Particulate," *J. Mat. Science: Mat. in Med.*, 9: 773–777(Kluwer Academic Publishers) 1998.

Coleman, J. J., et al., "Mandibular Reconstruction with Composite Microvascular Tissue Transfer", *Medline*, (*Abstract*) #91023289, 1991.

Freed, J. S., "Use of Injectable Biomaterials for the Repair and Augmentation of the Anal Sphincter", .*Chemical Abstract*, 119: #195701, 1993.

Fung, M. C. et al., "Silver Products for Medical Indications: Risk–Benefit Assessment", *J. Toxicol.*, 34(1): 119–126 (American Academy of Clinical Toxicology and European Association of Poisons Centres and Clinical Toxicologist) 1996.

Goldman Sachs/U.S. Research, "Advanced Tissue Sciences, (ATS)", (Healthcare: Biotechnology)1–30, 1996.

Greenspan, D. C., et al., "The Evaluation of Degradability of Melt and Sol–Gel Derived Bioglass® In Vitro", *Bioceramics*, 10: 391–394 (Published by Elsevier Science) 1997.

Greenspan, D. C., et al., "Bioactivity and Biodegradability: Melt vs. Sol–Gel Derived Bioglass® In Vitro and In Vivo" *Bioceramics*, 11: 345–348 (World Scientific Publishing Co.) 1998.

Grier, N., "Mercurials–Inorganic and Organic, Chapter 17" and "Silver and its Compounds, Chapter 18", *Disinfection, Sterilization and Preservation* 346–389 (Lea & Febiger, $3^{rd}$ ed.) 1983.

Guo, et al., "Preparation and Studies of Bioactive Glass", *Chemical Abstracts*, v.120: #144090, 1994.

Hench, L.. L.., , et al., *Biomaterials, An Interfacial Approach*, ( Academic Press, New York) 1982.

Hench, L. L., et al., "The Sol–Gel Glass Transformation of Silica", *Phase Transitions, A Multinational Journal*, 24–26: 785–834 (Gordon & Breach Science Publishers, S.A.)1990).

Hench, L. L. et al., "The Sol–Gel Process", *Chemical Reviews*, 90: 33–72 (American Chemical Society) 1990.

Hench, L. L., et al., "Biological Applications of Bioactive Glasses", *Life Chem. Rep.*, 13: 187–241 (Harwood Academic Publishers GmbH) 1996.

Hench, L. L., et al., "Introduction to Bioceramics, Chapter 1", *Advanced Series in Bioceramics*, 1: 1–24, (World Scientific) 1993.

Hench, L. L., et al., "Introduction to Bioceramics, Chapter 3", *Advanced Series in Bioceramics*, 3: 41–47, (World Scientific) 1993.

Hench, L. L., et al., "Introduction to Bioceramics, Chapter 4", *Advanced Series in Bioceramics*, 4: 63–79, (World Scientific) 1993.

Hench, L. L., et al., "Introduction to Bioceramics, Chapter 13", *Advanced Series in Bioceramics*, 13: 239–259, (World Scientific) 1993.

Hench, L. L., et al., "Introduction to Bioceramics, Chapter 18", *Advanced Series in Bioceramics*, 18: 319–334, (World Scientific) 1993.

Hench, L. L., et al., "Bonding Mechanisms at the Interface of Ceramic Prosthetic Materials",*J. Biomed. Mater. Res.*, 2: (1)117–141, (John Wiley & Sons, Inc.)1971.

Hench, L. L., "Bioactive Ceramics: Theory and Clinical Applications", *Bioceramics*, 7: 3–14 (Butterworth–Heinemann Ltd.) 1994.

Jansen, B., et al., "In vitro Evaluation of the Antimicrobial Efficacy and Biocompatibility of a Silver–Coated Central Venous Catheter", *J. Biomater. Appl*, 9(1): 55–70 (Technomic Publishing Co.) 1994.

Jansson, G., et al., "Stimulating Effects of Mercuric–and Silver Ions on the Superoxide Anion Production in Human Polymorphonuclear Leukocytes", *Free Rad. Res. Comms.*, 18(2): 87–98 (Harwood Academic Publishers GmbH) 1993.

Kawashita, M., et al., "Preparation of Antibacterial Silver-Containing Silica Glass by Sol–Gel Method," *Bioceramics*, 11: 703–706 (World Scientific Publishing Co.) 1998.

Keeting, P. E.,et al., "Zeolite A Increases Proliferation, Differentiation, and Transforming Growth Factor β Production in Normal Adult Human Osteoblast–Like Cells In Vitro", *J. Bone & Miner. Res.*, 7(11): 1281–1289 (Mary Ann Liebert, Inc.) 1992.

Kelton, P. L., MD, "Skin Grafts", *Selected Readings in Plastic Surgery*, 7(2): 1–25, (Baylor University Medical Center) 1992.

Kim, T. N., et al., "Antimicrobial Effects of Metal Ions ($A^+$, $Cu^2$, $Zn^{2+}$) in hydroxyapatite", *J. Mater. Sci.–Mat. Med.*, 9: 129–134 (Chapman & Hall) 1998.

Kokubo, T., et al., "Solutions Able to Reproduce in Vivo Surface–structure Changes in Bioactive Glass–Ceramic A–$W^{3}$", *J. Biomed. Mater. Res.*, 24:721–734 (John Wiley & Sons, Inc.) 1990.

Liau, S. Y., et al, "Interaction of Silver Nitrate with Readily Identifiable Groups: Relationship to the Antibacterial Action of Silver Ions", *Lett. Appl. Microb.*, 25: 279–283 (Published for the Society for Applied Bacteriology by Blackwell Science) 1997.

Loeffler, U., et al., "Kit for in Situ Formation of Topical Gel for Enzyme Release in Wounds" *Chemical Abstracts, 127: 140–572*, 1997.

Nogami, M. et al., "Glass Formation Through Hydrolysis of $Si(OC_2H_5)_4$ With $NH_4$ and HCI Solution", *J. Non–Chryst. Solids*, 37: 191–201 (North–Holland Publishing Co) 1980.

Pereira, M. M., et al., "Effect of Texture on the Rate of Hydroxyapatite Formation on Gel–Silica Surface", *J. Am. Chem. Soc.*, 78(9): 2463–2368, (Am. Ceramic Soc.) 1995.

Pereira, M. M., et al., "Homogeneity of Bioactive Sol–Gel Derived Glasses in the System $CaO-P_2O_5-SiO_2$", *J. Mater. Synth. Proces.*, 2(3):189–196 (Plenum Pub. Co. 1994.

Periera, M. M., et al., "Mechanisms of Hydroxyapatite Formation on Porous Gel–Silica Substrates", *J. Sol–Gel Sci. Technol,*, 7: 59–68 (Kluwer Academic Pub.)1996.

Pérez–Pariente, J., et al., "Influence of Composition and Surface Characteristics on the in Vitro Bioactivity of $SiO_2-CaO-P_2O_5-MgO$", *J. Biomed. Mater. Res.*, 170–175, (John Wiley &Sons, Inc.) 1999.

Rabinovich, E. M., et al., "Fluorine in Silica Gels", *Better Ceramics Through Chemisry II*, 251–259 (Brinker, Clark, Ulrich, eds, Materials Research Society, Pittsburgh, PA) 1986.

Reese, A. C., et al., "Role of Fibronectin in Wound Healing", *Current Advances in Oral and Maxillofacil Surgery*, 1: 1–25, (no date) Date unavailable.

Scalzo, M., et al., "Antimicrobial Activity of Electrochemical Silver Ions in Nonionic Surfactant Solutions and in Model Dispersions", *j. Pharm. Pharmacol.*, 48(1): 60–63 (The Royal Pharmaceutical Society of Great Britain) 1996.

Shapiro, L., et al., "Ciliary Neurotrophic Factor Combined with Soluble Receptor Inhibits Synthesis of Proinflammatory Cytokines and Prostaglandin-$E_2$ in Vitro" *Exp. Cell. Res.,*, 215 (1): 51–56, (Academic Press, Inc.) 1994.

Shirkanzadeh, M., et al., "Formation of Carbonate Apatite on Calcium Phosphate Coatings Containing Silver Ions," *J. Mat. Science, Mat. in Medicine*, 9: 385–389 (Kluwer Academic Publishers) 1998.

Slawson, R. M., et al., "Germanium and Silver Resistance, Accumulation, and Toxicity in Microorganisms" *Plasmid*, 27(1): 72–79 (Bimonthly by Academic Press, Inc.)1992.

Stoor, P., et al., "Interactions Between the Frontal Sinusitis–Associated Pathogen *Haemophilus Influenza* and the Bioactive Glass S53P4", *Bioceramics*, 8: 253–258 (Pergamon) 1995.

Stoor, P. et al., "Antibacterial Effects of a Bioactive Glass Paste on Oral Microorganisms", *Acta Odontol. Scand.*, 56:161–165 (Scandinavian University Press) 1998.

Theilmann, et al, "Two –Layer Bandage Made of a Polymer and a Water–absorbing Material", *Chemical Abstracts* 112: 240557, 1990.

Ulich, T. R., et al., "Intratracheal Injection of LPS and Cytokines, V. LPS Induces Expression of LIF and LIF Inhibits Acute Inflammation", *Am. J. Physiol.*, 267 (4, pt. 1/2): L442–446 (The Am. Physiological Soc.) 1994.

von Nägeli, C., "Tötliche Wirkung von angeblich reinem Wasser auf lebende Zellen", *Denkschriften der Schweiz Naturforsch. Ges.*, 33:1–10, 1893.

Vrouwenvelder, C. A., et al., "Histological and Biochemical Evaluation of Osteoblasts Cultured on Bioactive Glass, Hyudroxylapatite, Titanium Alloy, and Stainless Steel", *J. Biomed. Mater. Res.*, 27: 465–475 (John Wiley & Sons, Inc.) 1993.

Warren, L. D., et al., "An Investigation of Bioglass Powders: Quality Assurance Test Procedure and Test Criteria", *J. Biomed Mater. Res.*, 23(A2): 201–209 (John Wiley & Sons, Inc.) 1989.

Wells, T. N. C., et al, "Mechanism of Irreversible Inactivation of Phosphomannose Isomerases by Silver Ions and Flamazine", *Biochemistry*, 34(24): 7896–7903 (American Chemical Society) 1995.

Wood, S, "Case Study: Traumatic Pressure Sore of the Left Lateral Malleolus", *Medline*, (*Abstract*) 9315 543, 1993.

Wright, J. B., et al., "The Comparative Efficacy of Two Antimicrobial Barrier Dressings: In–vitro Examination of Two Controlled Release of Silver Dressings," *Wounds: A Compendium of clinical Research and Practice*, 10(6): 179–188, (Westaim Biomedical Corp.)1998.

Zhong, J., et al., "Porous Sol–Gel Bioglass® From Near–Equilibrium Drying", *Bioceramics*, 10, 265–268 (Elsevier Science) 1997.

* cited by examiner

ANTI-INFLAMMATORY AND ANTIMICROBIAL USES FOR BIOACTIVE GLASS COMPOSITIONS

This application is a continuation-in-part of Ser. No. 09/164,293, filed Oct. 1, 1998, now U.S. Pat. No. 6,428,800, which is a continuation of Ser. No. 08/715,911, filed Sep. 19, 1996, now U.S. Pat. No. 5,834,008, and this application is a continuation of Ser. No. 09/392,516, filed Sep. 9, 1999, abandoned, which claims priority to Ser. No. 60/099,725, filed Sep. 10, 1998.

FIELD OF THE INVENTION

The present invention relates to bioactive glass-containing compositions, aqueous extracts derived from such compositions, cosmetics including these compositions, implants including the compositions, and methods of using the compositions to accelerate healing, reduce inflammation and reduce bacterial infection. More specifically, the present invention relates to compositions including particles of bioactive glass, optionally including one or more agents which aid in the delivery and distribution of the particles and which may also have other therapeutic effects, and methods of use thereof.

BACKGROUND OF THE INVENTION

When an injury occurs, cell damage initially comes from the precipitating event, such as a cut, resulting in ruptured cells and severed or crushed capillaries and other blood vessels. However, later damage can occur due to bacterial growth or to an inflammatory response.

The healing process involves several steps, including coagulation, inflammation, repair (or fibroplasia) of the damaged tissue, angiogenesis (or revascularization), re-epithelialization and remodeling. Several of these steps, while necessary to promote normal healing, can cause excessive scarring and other health related problems if unchecked.

For example, unchecked inflammation can have harmful consequences. For example, many chronic and even life-threatening disorders, such as asthma, rheumatoid arthritis, lung fibrosis, peritoneal adhesions, hypersensitivity and autoimmune diseases are a result of an uncontrolled inflammatory response. An unresolved inflammation in the lung resulting from bacterial infection (i.e., pneumonia) may eventually lead to extensive tissue damage and a chronic lung abscess. Inflammation of the peritoneal cavity and the resulting adhesions following abdominal surgery is a major cause of infertility in women. Asthma is an often life-threatening disorder which results from an inadvertently stimulated inflammatory response in the lungs.

An excessive inflammatory response can cause extensive swelling, which can lead to additional injury as a result of anoxia. Pain results from a combination of kinins and the effect of lysozymes and pressure from the swelling on nerve endings. Unchecked, the inflammatory response can set off a neural feedback loop and cause hyperalgesia, a phenomenon in which the surrounding area of injury remains painful. Accordingly, there is a great interest in the medical community to develop anti-inflammatory agents.

The amount of bacterial burden in a wound bed is an important factor in the healing of wounds, especially dermal ulcers. Some bacterial colonization is inevitable, and may even be beneficial in stimulating the body's natural immune response. However, excessive bacterial colonization is clearly detrimental and can lead to high levels of bacterial waste products, chronic inflammation, heavy exudate, increased tissue necrosis and eventually, full infection. Wounds typically will not heal when the bacterial burden is above about $10^5$ microorganisms per gram of tissue.

Topical anti-microbial agents, including organism specific antibiotics such as bacitracin and silver sulfadiazine are typically used in wound care. However, these agents are generally regarded as relatively weak in action. More importantly, the recent rise of strains of microorganisms resistant to these agents has led to many intractable cases of infection. Other typically used antimicrobial agents, such as iodine and alcohol, damage native tissue and repair cells, and retard the healing process of dermal wounds.

Many treatments have been proposed for treating wounds and accelerating wound healing. Often, such treatments involve the use of growth factors, such as platelet derived growth factor (PDGF) or the use of cultured cells derived from the wounded patient's own skin. These methods are limited by the difficulty of preparing the growth factors, the time spent in preparing the cell cultures, and the high costs of such treatments. Further, potential side effects associated with such therapies are unknown at this time. For example, the prolonged use of corticosteroids is associated with untoward secondary effects.

It would be advantageous to provide compositions and methods for treating wounds, and, in particular, for treating bacterial infection and inflammatory response in patients. The present invention provides such compositions and methods.

SUMMARY OF THE INVENTION

Compositions and methods for treating wounds to significantly reduce the healing time and prevent the body's natural defenses from proceeding unchecked are disclosed. The compositions and methods allow wounds to heal in significantly less time than would otherwise occur. Inflammation is greatly reduced around the wound site. The incidence of scar formation following a wound or burn is reduced. The presence of bacteria is also reduced. The success of skin grafts is increased.

The compositions include non-interlinked particles of bioactive glass, alone or in combination with an additional anti-bacterial and/or anti-inflammatory agent, and optionally include other therapeutic agents. Formulations including the compositions, alone or in combination with a suitable carrier, preferably for topical administration, are also disclosed. Also disclosed are anti-bacterial solutions derived from bioactive glass, and methods of preparation and use thereof.

The compositions can be incorporated into implanted materials, such as prosthetic implants, sutures, stents, screws, plates, tubes, and the like, to impart anti-bacterial and anti-inflammatory properties to the materials. Anti-bacterial properties can also be imparted to devices used for in vitro and ex vivo cell culture by incorporating the composition into the devices.

Anti-bacterial and anti-inflammatory compositions derived from aqueous extracts of bioactive glass can be formed by placing bioactive glass in an aqueous solution, allowing the glass to dissolve over a suitable period of time, for example, a week or more, and filtering out the undissolved glass particles. The solvent can also be evaporated to provide a solid material with anti-bacterial properties. These compositions can be used in situations where prevention or reduction of bacterial infections would be advantageous, for example, food preparation, cosmetics, media used for cell culture, and buffer solutions.

When used topically to treat a wound or burn, the wound or burn is contacted with an effective amount of the composition for the intended application. When used for skin grafting, the bioactive glass-containing composition is applied to either the graft site prior to placing the donor tissue, or to the donor tissue itself.

The compositions can be administered to the pulmonary system, for example, via an inhaler, as an adjunct therapy for treating pneumonia or chronic sinus infections. The compositions can also be co-administered to the pulmonary system with therapeutic agents which are themselves inflammatory, to minimize the inflammatory response to these agents. The compositions can be applied directly to a surgical site to minimize post-surgical adhesions, minimize inflammation around the site, and prevent or minimize infection at the site. In one embodiment, the compositions are included in a polymeric material, preferably a biodegradable polymeric material, which is then applied to a surgical site to minimize post-surgical adhesions.

DETAILED DESCRIPTION OF THE PREFERRED EMBODIMENTS

Compositions and methods for treating wounds to significantly reduce the healing time and prevent the body's natural defenses from proceeding unchecked are disclosed. The compositions and methods allow wounds to heal in significantly less time than would otherwise occur. Inflammation is greatly reduced around the wound site. The incidence of scar formation following a wound or burn is reduced. The presence of bacteria is also reduced. The success of skin grafts is increased.

The compositions include non-interlinked particles of bioactive glass, alone or in combination with an additional anti-bacterial and/or anti-inflammatory agent, and optionally include other therapeutic agents. Formulations including the composition and a suitable carrier, preferably for topical administration, are also disclosed. Also disclosed are anti-bacterial solutions derived from bioactive glass, and methods of preparation and use thereof.

Not being bound to any particular theory or mechanism, it is believed that the surface area and reactivity of particulate bioactive glass provides an adsorption of hydronium ions from a solution and a release of sodium that increases the pH of the environment. Through the pH-dependent binding of hemoglobin, the amount of oxygen in the wound or burn is thereby increased.

These reactions also cause a higher negative surface charge on the glass surface and the development of a high specific surface area (e.g. from 0.5 $m^2/g$ initially to over 50 $m^2/g$ by 12 hours) which attracts collagen fibrin, fibronectin and cells. Moreover, the bioactive glass provides for the precipitation of calcium and phosphorous naturally present in the wound exudate and blood which cause the rapid formation of a calcium phosphate layer that may incorporate collagen, fibrin and fibronectin to stabilize the wound quickly and effectively. In addition, the bioactive glass is believed to strongly inhibit the overactive inflammatory response present in chronic wounds. In some cases, wounds or burns healed with the compositions and methods disclosed herein heal without the necessity of eschar formation. That is, new epithelial tissue can be directly formed. The bioactive glass-containing compositions described herein have been shown to increase the IL-6 concentration when injected into the peritoneal cavity of mice, without a concomitant increase in other cytokines, such as TNF-α, IL-1 and IL-10. The absence of the other cytokines indicates that the overall response is anti-inflammatory rather than pro-inflammatory.

The terms "wound" and "burn," collective referred to herein as "injury" have their usual meanings. "Normal" is used in the sense it is usually used in the medical arts. The terms "anti-bacterial agents" and "antibiotics" as used herein mean pharmacologically acceptable synthetic or natural agents which destroy or inhibit microorganisms and includes both antibacterial and antiviral agents. "Medical practitioner" means one of ordinary skill in the art wound and burn treatment. Typically this person is a physician, nurse, dentist, or paramedic.

I. Compositions Including Bioactive Glass

Compositions including non-interlinked particles of bioactive glass, alone or in combination with anti-bacterial agents and/or anti-inflammatory agents, can be used for a variety of purposes.

As used herein the terms "bioactive glass" or "biologically active glass" mean an inorganic glass material having an oxide of silicon as its major component and which is capable of bonding with growing tissue when reacted with physiological fluids.

Bioactive glasses are well known to those skilled in the art, and are disclosed, for example, in *An Introduction to Bioceramics*, L. Hench and J. Wilson, eds. World Scientific, New Jersey (1993), the contents of which are hereby incorporated by reference.

The glass preferably includes between 40 and 86% by weight of silicon dioxide oxide ($SiO_2$), between about 0 and 35% by weight of sodium oxide ($Na_2O$), between about 4 and 46% by weight calcium oxide (CaO), and between about 1 and 15% by weight phosphorus oxide ($P_2O5$). More preferably, the glass includes between 40 and 60% by weight of silicon dioxide oxide ($SiO_2$), between about 5–30% by weight of sodium oxide ($Na_2O$), between about 10 and 35% by weight calcium oxide (CaO), and between about 1 and 12% by weight phosphorus oxide ($P_2O5$). The oxides can be present as solid solutions or mixed oxides, or as mixtures of oxides.

$CaF_2$, $B_2O_3$, $Al_2O_3$, MgO and $K_2O$ may be included in the composition in addition to silicon, sodium, phosphorus and calcium oxides. The preferred range for $B_2O_3$ is between 0 and 10% by weight. The preferred range for $K_2O$ is between 0 and 8% by weight. The preferred range for MgO is between 0 and 5% by weight.

Anti-microbial salts such as $AgNO_3$, CuO, and ZnO, or other antimicrobial salts of the silver, copper and zinc ions, such as nitrates, acetates, etc., can be added. The preferred range for these salts is between 0 and 5% by weight.

The most preferred glass is Bioglass®™ (a trademark of University of Florida), which has a composition including about 45% by weight silicon dioxide, about 24.5% by weight sodium oxide, about 6% by weight phosphorus oxide, and about 24.5% by weight calcium oxide. Another preferred material is hydroxyapatite.

Particulate, non-interlinked bioactive glass is preferred in the present invention. That is, the glass is in the form of small, discrete particles, rather than a fused matrix of particles or a mesh or fabric (woven or non-woven) of glass fibers. Note that under some conditions the discrete particles of the present invention may tend to cling together because of electrostatic or other forces but are still considered to be non-interlinked. Preferably the particle size is less than about 90 microns; more preferably, less than about 20 microns; even more preferably, less than about 5 microns, and ideally, less than about 2 microns, as measured by SEM or laser light scattering techniques.

Highly porous bioactive glass has similar anti-bacterial and anti-inflammatory properties to small particles of bioactive glass, due to its relatively fast degradation rate and high surface area, in comparison to non-porous bioactive glass compositions. When highly porous bioactive glass is used in place or in addition to small particles of bioactive glass, the pore size is between about 0 and 500 $\mu$m, preferably between about 10 and 150 $\mu$m, and more preferably, between about 50 and 100 $\mu$m. The degree of porosity of the glass is between about 0 and 85%, preferably between about 30 and 80%, and more preferably, between about 40 and 60%. Porous bioactive glass can be prepared, for example, by incorporating a leachable substance into the bioactive glass composition, and leaching the substance out of the glass. Suitable leachable substances are well known to those of skill in the art, and include, for example, sodium chloride and other water-soluble salts. The particle size of the leachable substance is roughly the size of the resulting pore. The relative amount and size of the leachable substance gives rise to the degree of porosity. Also, as described herein, porosity can be achieved using sintering and/or by controlling the treatment cycle of glass gels to control the pores and interpores of the material.

The glass composition can be prepared in several ways, to provide melt-derived glass, sol-gel derived glass, and sintered glass particles. The sintered particles may be in sol-gel derived, or pre-reacted melt derived form. Sol-gel derived glass is generally prepared by synthesizing an inorganic network by mixing metal alkoxides in solution, followed by hydrolysis, gelation, and low temperature (around 200–900° C.) firing to produce a glass. Sol-gel derived glasses produced this way are known to have an initial high specific surface area compared with either melt-derived glass or porous melt-derived glass. The surface area of the sol-gel derived glasses is at least about 50 $m^2/g$. Melt derived glass is generally prepared by mixing grains of oxides or carbonates, melting and homogenizing the mixtures at high temperatures, typically between about 1250 and 1400° C. The molten glass can be fritted and milled to produce a small particulate material.

The glass composition is preferably melt-derived. In each preparation, it is preferred to use reagent grade glass, especially since the glass is used to prepare materials which ultimately may be administered to a patient.

A. Melt Derived Glass

A melt-derived glass composition can be prepared, for example, by preparing an admixture of the individual metal oxides and other components used to prepare the glass composition, blending the admixture, melting the admixture, and cooling the mixture. The melting temperature is determined in large part by the glass composition, and ranges, for example, from about 900–1500° C., preferably between about 1250 and 1450° C. The melt is preferably mixed, for example, by oxygen bubbling, to ensure a thorough homogenation of the individual components.

The mixture can be cooled, for example, by adding the molten admixture to a suitable liquid, such as deionized water, to produce a glass frit. Porosity can be introduced by grinding the glass into a powder, admixing the powder with a foaming agent, and hot pressing the mixture under vacuum and elevated temperature. The particle size of the glass powder is between about 2 and 70 $\mu$m, the vacuum is preferably less than 50 MPa, and the hot pressing is preferably performed at a temperature above 400° C., preferably between about 400 and 500° C. Suitable foaming agents include compounds which evolve carbon dioxide and/or water at elevated temperatures, for example, metal hydroxides, metal carbonates, and peroxides, such as hydrogen peroxide. Preferred metal carbonates are sodium bicarbonate, sodium carbonate and calcium carbonate. The foaming agents are preferably added in a range of between about 1–5, more preferably 2–3 percent by weight of the glass powder. The preparation of melt-derived porous glass is described, for example, in U.S. Pat. No. 5,648,301 to Ducheyne and El Ghannam, the contents of which are hereby incorporated by reference.

B. Sintered Glass Particles

Glass can be sintered using known methodology. In one embodiment, an aqueous slurry of the glass powder and a foaming agent with a suitable binder, such as polyvinyl alcohol, is formed. The slurry is then poured into a mold, allowed to dry, and sintered at high temperatures. These temperature may range, depending on the glass composition and foaming agent used, between about 500 and 1000° C., more preferably between about 600 and 800° C.

C. Spun Fibers of Sol-gel Derived Glass

It is known in the art to control the heat treatment cycle of glass gels to control the pores and interpores of the material to create a porous glass material. However, since a pore diameter larger than 0.1 microns is difficult to achieve using this method, the sintering and foaming processes described herein are generally more preferred.

D. Leaching of the Porous Material

To aid in preparing glass compositions with high porosity, the glass composition can include a material which can be preferably leached out of the glass composition, and, in doing so, provide the composition with high porosity. For example, minute particles of a material capable of being dissolved in a suitable solvent, acid, or base can be mixed with or melted into the glass, and subsequently leached out. The resulting voids have roughly the same size as the particle that was leached out. In the case of a material which is part of a melt-derived glass composition, the size of the pores and degree of porosity depends on the amount of added material relative to the amount of glass. For example, if the leached material constituted about 80% of the glass, then the glass would be approximately 80% porous when the material was leached out. When leaching the glass composition, care should be taken not to leach out those components which add to the bioactivity of the glass, i.e., the calcium and phosphorus oxides.

II. Formulations Including Bioactive Glass

The bioactive glass may be administered to the wound in a topical, pharmaceutical formulation, such as in the form of a suspension, lotion, cream, ointment, or gel. Those skilled in the art will appreciate that there are other appropriate topical carriers such as those listed in U.S.P.D.

Other Therapeutic Agents

In addition to bioactive glass, the formulations can include other therapeutic agents such as antibiotics, antivirals, healing promotion agents, anti-inflammatory agents, immunosuppressants, growth factors, antimetabolites, cell adhesion molecules (CAMs), bone morphogenic proteins (BMPs), vascularizing agents, anticoagulants, and topical anesthetics/analgesics.

The antibiotics can be topical antibiotics suitable for skin treatment. Examples of such antibiotics include but are not limited to: chloramphenicol, chlortetracycline, clyndamycin, clioquinol, erythromycin, framycetin, gramicidin, fusidic acid, gentamicin, mafenide, mupiroicin, neomycin, polymyxin B, bacitracin, silver sulfadiazine, tetracycline and chlortetracycline.

Suitable antivirals include topical antivirals, such as acyclovir, and gancyclovir. Suitable anti-inflammatory agents include corticosteroids, hydrocortisone and nonsteroidal antinflammatory drugs. Suitable growth factors include basic fibroblast growth factor (bFGF), epithelial growth factor (EGF), transforming growth factors α and β (TGF α and β), platelet-derived growth factor (PDGF), and vascular endothelial growth factor/vascular permeability factor (VEGF/VPF)). Suitable topical anesthetics include benzocaine and lidocaine.

In one embodiment, the therapeutic agent is one which would otherwise cause an inflammation at the site at which it is delivered, and the bioactive glass particles reduce the associated inflammation. For example, a number of compounds, for example, amine compounds, result in inflammation when administered topically, i.e., in a transdermal patch. A number of other compounds result in inflammation when administered via pulmonary administration, i.e., via an inhaler.

It is acceptable to place particulate bioactive glass directly into a wounded area or on a burn with no carrier or excipient. However, preferably bioactive glass alone or in combination with one or more other therapeutic agents is combined in any pharmaceutically acceptable carrier for topical use, such as a suspension, ointment, cream, or gel to facilitate application to the wound. For example, the composition of the present invention can be blended with white petrolatum to form an ointment, with mineral oil to form a suspension, with a commercially available, cream cosmetic base to form a non-greasy cream, or with a commercially available water soluble, lubricating gel, e.g., K Y Gel (trademark), to form a high moisture gel.

The bioactive glass and other therapeutic agents can be combined with other wound and burn treatments or dressings such as, but not limited to, collagen, fibrin, fibronectin, various growth factors, such as PDGF, TGF-β, vitamin E, gauze, cotton, cellulose, synthetic wound or burn dressings and other wound or burn dressings/treatments known to those of ordinary skill in the art. Dressings of fiberglass, including fiberglass made from fibers of bioactive glass, can also be used. In addition, the bioactive glass may be combined with any biocompatible material, such as biodegradable polymer like polylactic/glycolic acid to form a composite material for accelerating would healing.

While the ratio of bioactive glass to carrier is not critical, preferably the blend of bioactive glass, other therapeutic agents, and carrier contains about 20% to about 80% bioactive glass. The preferred particle size range for the bioactive glass not greater than about 90 microns is recommended. Particle sizes specifically less than about 10 microns as well as less than about 2 microns can also be used, where the particle sizes are measured by SEM or laser light scattering techniques. Particles of such a small size range generally provide for the advantages of the present invention but do not illicit any undesirable immune response. This phenomenon is an unanticipated result, given the general history found in the literature on the biological response to small synthetic particles. The proportion other therapeutic agents varies according to the agent and the nature of the application. However, the preferred proportions are such that the amount of the agent administered to the wound or burn is in the dosage range accepted within standard medical care.

If the bioactive glass is to mixed with a topical carrier such as an ointment, then it is preferable that the glass not be significantly pre-reacted prior to application. This can be achieved, for example, by applying the composition immediately after mixing. Alternately, the topical carrier may be of such a nature as to not pre-react the glass, such as, for example glycerin. The bioactive particulate glass and topical carrier can be separate components in a two part system wherein the bioactive glass and topical carrier are mixed and simultaneously applied. For example, a two part mixing syringe with two separate storage chambers and a mixing chamber can be used. Other two part systems could also be used. For example, the particulate bioactive glass can be incorporated into a bandage and the topical carrier can be applied to the wound or burn which is followed by application of the bandage. Other two part delivery systems are known to those of ordinary skill in the art.

III. Articles of Manufacture Including Bioactive Glass

The compositions can be incorporated into implanted materials, such as prosthetic implants, sheets, pins, valves, sutures, stents, screws, plates, tubes, and the like, by incorporating bioactive glass particles into the implanted materials. The compositions can be moldable or machinable.

In another embodiment, anti-bacterial properties are imparted to devices used for in vitro and ex vivo cell culture by incorporating non-interlinked particles of bioactive glass into the devices.

The articles of manufacture are imparted with antibacterial properties via the incorporation of the bioactive glass, which will allow the articles to be implanted, or used to culture cells, with a reduced likelihood of bacteriological contamination.

IV. Aqueous Solutions Derived from Bioactive Glass

The anti-bacterial (and anti-fungal) compositions derived from aqueous extracts of bioactive glass are formed by placing bioactive glass in an aqueous solution, allowing the glass to dissolve over a suitable period of time, and filtering out the undissolved glass particles. The solvent can be evaporated to provide a solid material with anti-bacterial properties. The compositions can be used in situations where bacteria are present, for example, food preparation, solutions used for cell culture, and buffer solutions.

Without being bound to a particular theory, it is believed that there is a complex relationship between the type of ion being released from the glass, the amount of that ion, the rate at which release occurs, the pH of the solution, and the resulting anti-microbial or anti-inflammatory response. This effect is observed with respect to the particles of bioactive glass themselves and also in the ionic solutions derived from the glass particles. Accordingly, in the uses described below, particles of bioactive glass can be used in place of or in addition to the solutions derived from the particles.

Food Preparation

Numerous foods are potentially infected with bacteria, such as E. coli. Ground beef and chicken are particularly susceptible to bacterial infection. Aqueous solutions including an aqueous extract from bioactive glass have antibacterial properties. As discussed below in Example 3, the anti-bacterial effect is due, in part, to the basic nature of the solution (pH greater than about 7, preferably greater than about 9, more preferably greater than about 10.5). However, sodium hydroxide solutions of relatively high pH are not as effective at killing bacteria. Accordingly, the solutions have additional antibacterial elements present than merely a relatively high pH.

The composition can be sprayed on contaminated surfaces, or incorporated into food products such as ground beef. Since bioactive glass has been approved for various uses by the FDA, the extract of bioactive glass should be harmless to humans.

Cosmetic Applications

Liquid-based cosmetics, such as skin lotions, shampoos and rinses, are directly applied to human skin. While current manufacturing processes generally control bacterial contamination when the products are in sealed containers, after unsealing the package, bacteria, fungi and/or mold may contaminate the cosmetics. Often, various antibacterial agents are added to the cosmetics to minimize this process.

The compositions can be included in cosmetic applications to minimize contamination by bacteria, fungi and/or mold. The compositions can be added, for example, to cosmetic bases such as liquid foundation, shampoo, rinse, lipstick, skin lotion, milky lotion, creams and the like. The cosmetics can include the ionic solutions described herein and/or particles of bioactive glass described herein.

Solid Compositions

The aqueous solutions can be dried, for example, by spray drying or by drying in vacuo to provide an antibacterial composition. The compositions can be incorporated into other bacterial solutions, such as Betadine® solution, to provide an additional anti-bacterial component to the solutions.

Cell Growth and Culture

There are many solutions used for culturing cells. These include Dulbecco's minimal essential media, Hank's balanced salt solution, and others. These solutions are essentially isotonic with the cells to be cultured. A problem associated with cell culture is often the growth of bacteria in culture along with the desired cells. Bacterial growth can be minimized by incorporating the extract of bioactive glass into the cell culture media.

Buffer Solutions

Buffer solutions, such as HEPES and TRIS, are often at the perfect pH to support bacterial growth. Addition of the extract of bioactive glass to the compositions will impart anti-bacterial properties to the solutions. While the antibacterial effect of the extract solution is due in part to the relatively high pH, lower pH's are also somewhat effective. As shown in Example 3, even a pH of 7.6 was moderately effective as an anti-bacterial solution. Accordingly, although the buffer solutions will lower the pH somewhat, the solutions will still exhibit anti-bacterial properties. In one embodiment, the buffered solution is an i.v. solution, for example, phosphate buffered saline.

V. Methods for Improving Wound Healing

Particulate bioactive glass is capable of dramatically reducing the amount of time necessary for wound healing to occur. Further, a composition including non-interlinked particles of bioactive glass (or an implant including highly porous bioactive glass) and other anti-bacterial agents augments the natural healing process. The effectiveness of the composition is most dramatically illustrated in immune compromised patients whose ability to heal wounds is somewhat suppressed.

The compositions can be administered to a wound or burn in a similar manner as topical formulations currently in clinical use. The exact amount of application is at the discretion of the medical practitioner but is typically applied by generously spreading the composition into the desired area and placing a thin film on the surrounding area at least once a day. After application of the composition, the injured area is treated according to accepted medical practice. For example, after applying the composition, the injured area is typically covered with a sterile bandage, and the patient may be given antibiotics, analgesics and/or other medications systemically. Treatment of the injured area is continued until, in the judgement of the attending medical practitioner, the injury has healed and further treatment is not needed.

The methods for causing effective wound healing or providing an anti-bacterial treatment to wounds, involve contacting a wound with an effective wound healing or anti-bacterial amount of non-linked particles of bioactive glass, optionally in combination with an addition anti-bacterial or anti-inflammatory agent.

In one embodiment, the compounds are used to fill voids, including voids created during medical procedures. For example, during a root canal operation, the hollowed-out tooth can be filled with a composition including bioactive glass. This will help prevent bacterial infection until the tooth is ultimately filled. Also, bioactive glass-containing compositions can be used to fill the pockets that can develop between the teeth and gums. Compositions including bioactive glass can be used to fill voids present in aneurysms, and prevent bacterial growth inside the filled void. Other voids which can be filled include those formed surgically, such as removal of a spleen, ovary, gall bladder, or tumor.

VI. Methods for Grafting Skin

The methods for grafting skin involve applying non-linked particles of bioactive glass to either the graft site prior to placing the donor tissue, or to the donor tissue itself.

The methods for grafting skin involve applying particulate bioactive glass to either the graft site or donor tissue before it is placed in its intended location. Those interested in a detailed description of skin grafting are referred to "Skin Grafts," in *Selected Readings in Plastic Surgery*, vol. 7, No. 2, P. L. Kelton, MD, Baylor University Medical Center (1992). The graft may also be further treated with a topical carrier prior to placement. The application of bioactive glass to grafts is intended to increase the likelihood that the graft will "take" and incorporate in the host bed. It is intended that the bioactive glass particulates will act as an intermediary bond between the host and graft tissue, suppress the overall inflammatory response which could lead to rejection, as well accelerate the overall healing process which will lead to a faster and more successful acceptance.

VII. Methods for Improving the Appearance and Structure of Scar Tissue

The methods for improving the appearance and structure of scar tissue, especially keloid scar tissue, formed as a wound heals, involve contacting a wound as it heals with an effective scar appearance-improving amount of non-linked particles of bioactive glass. In this method, the particles are preferably present in a sterile, pharmaceutically acceptable carrier such as an ointment or gel.

The presence of a bioactive glass particulate within the healing wound bed may alter the formation of scar tissue by at least two mechanisms. First, bioactive glasses will act to reduce the overall inflammatory response in the wound through the adsorption of inflammatory mediators such as prostaglandins, TNF-$\alpha$, IL-1 and a variety of cytokines and the release of ions that leads to an increase in extracellular osmotic pressure. A reduced inflammatory response will decrease the number and activity of macrophages and other inflammatory cells, thereby reducing the concentration of chemotactic molecules released to recruit fibroblasts. The end result of decreased fibroblast activity from otherwise overactive levels is a reduction in the density of scar tissue.

Secondly, bioactive glasses attract and bind collagen fibers to their surface. As fibroblasts infiltrate the wound they migrate among the glass particulate and lay down collagen among and on the surface of the particles. The random distribution of bioactive glass particles to which collagen fibers are attracted and attached will determine that the fibers themselves are randomly oriented. As the glass particles resorb, they leave behind a bed of randomly oriented collagen fibers whose mechanical properties more closely match those of unwounded tissue.

An added benefit of using the above methods for treating wound and grafting skin is that the scar tissue formed upon healing is more uniform and more closely matches the surrounding skin. Thus, the scar tissue, the formation of which is generally unavoidable, has a better appearance. This benefit is particularly important for treating wound and burns on the face. The compositions can also be used to improve the appearance and structure of scar formed as the wound or burn heals.

VIII. Methods of Reducing Inflammation

The compositions can be used to reduce inflammation in a patient. Overly acute or chronic inflammation can result in various disease states in a patient, for example, arthritis and tendinitis, pulmonary disorders such as asthma and emphysema, and post-surgical (peritoneal) adhesions.

Very small particulate bioactive glass has the property of exerting an anti-inflammatory effect when in contact with body tissue. It appears that the bioactive glass suppresses the production of tissue necrosis factor alpha (TNF-$\alpha$) and interleukin-1 (IL-1) at the earliest stages of administration of the bioactive glass. This effect is transient and does not induce any secondary immunologic response. This is very different than the administration of growth factors, antibiotics or other cytokines that all show secondary effects on the immune system, even though they may be small.

TNF-$\alpha$ is a powerful pro-inflammatory cytokine that not only participates in the normal inflammatory response, but is also implicated in myocardial dysfunction and cardiomyocyte death in ischemia-reperfusion injury, sepsis, chronic heart failure, viral myocarditis and cardiac allograft rejection, as well as a host of other inflammatory disorders. Accordingly, by suppressing the production of TNF-$\alpha$, the compositions reduce the likelihood of these disorders occurring.

The preferred size range for the bioactive glass, for this embodiment, is such that the particles do not physically obstruct vascular, lymph or pulmonary pathways as the particles pass through the body. Particles less than 20 microns in size, as measured by SEM or laser light scattering techniques, are particularly preferred, as immunochemistry results indicate that the body does not respond to these particles as it would to other particles, for example, silica particles. Experiments have shown that the body does not show abnormal or elevated recruitment of macrophages to the area where Bioglass® particles have been injected. This is in stark contrast to small particles of other materials, such as talcum, asbestos, silicone and metal debris, which are known to be strongly pro-inflammatory.

While not intending to be bound to any particular theory or mechanism, it is believed that the high surface area and reactivity of the particulate bioactive glass provides for the release of soluble sodium, calcium, phosphate, silica and other ionic species. The ionic environment, alone with the increased pH, is believed to act in such a way as to affect the expression of important cellular mediators of inflammation. In addition, direct contact of neutrophils, macrophages and other immune cells with the particle surface may elicit an unexpected an anti-inflammatory effect on cell function.

Incorporation of the anti-inflammatory bioactive glass particles into compositions intended for pulmonary delivery of therapeutic agents can be beneficial when those agents cause inflammation in the lung after delivery.

Topical inflammatory effects, such as those observed in some patients using transdermal patches, can be alleviated by incorporating bioactive glass particles into a topical formulation, such as a gel, creme, foam, lotion, or transdermal patch.

Numerous efforts have been made to deliver drugs via the pulmonary tract. Several therapeutic agents cause local inflammatory effects when delivered. These effects can be minimized by incorporating bioactive glass particles into the compositions for pulmonary administration. In one embodiment, an aqueous extract of bioactive glass can be used in place of or in addition to the bioactive glass particles to cause the same anti-inflammatory effect. The aqueous solution can be used as a pharmaceutical carrier in an intra-nasal drug delivery device.

Particles of bioactive glass, and/or solutions including the extract from bioactive glass, can be delivered by local injection to sites of inflammation in a patient, for example, at an inflamed joint or tendon.

Particles of bioactive glass, and/or solutions including the extract from bioactive glass, can be delivered by intravenous, intramuscular, or intra peritoneal injection to provide systemic anti-inflammatory effects. These effects can be therapeutic and/or prophylactic. For example, systemic delivery of bioactive glass, and/or solutions including the extract from bioactive glass, can be effective in reducing the onset of inflammation brought on by external challenge.

Particles of bioactive glass can be administered locally to a surgical site to minimize post-surgical adhesions. The glass particles can optionally be incorporated into a polymeric material which is applied to the surgical site. Preferably, the polymeric material is biodegradable, and the particles are released as the polymer degrades. Suitable polymeric materials for this purpose are disclosed, for example, in U.S. Pat. No. 5,410,016 to Hubbell et al., the contents of which are hereby incorporated by reference. Other materials suitable for this purpose, such as Interceed®, agarose and crosslinked alginate, are well known to those of skill in the art.

Highly porous bioactive glass can have the same anti-inflammatory effects as the small glass particles, due to its relatively high surface area.

Biomedical implants are often associated with inflammation at the site of implantation. Incorporation of small particles of bioactive glass and/or highly porous bioactive glass into the implants, especially on the surface of the implants, can greatly reduce the inflammation associated with the implants. This can be especially useful in suture materials to minimize the inflammation associated with these materials. As discussed below, the anti-bacterial properties of the compositions also allow the sutures to minimize the infection surrounding the suture site.

An "effective, anti-inflammatory amount of bioactive glass" refers to an amount of bioactive glass, with an appropriate particle size, which is effective at reducing the inflammation. Those of skill in the art can readily estimate the actual or anticipated inflammation associated with a wound site, for example, caused by an injury, a surgical procedure, arthritis or other autoimmune disorders, by administration of a therapeutic agent to the pulmonary system or to the skin, for example, via a transdermal delivery system, and the like. Those of skill in the art can also use this estimate to determine an appropriate anti-inflammatory amount of bioactive glass to administer to the inflamed site, or site of anticipated inflammation.

IX. Methods of Reducing Bacterial Infection

Large particles of bioactive glass and non-porous bioactive glass do not have appreciable bactericidal properties. However, small particles of bioactive glass and highly porous bioactive glass, when present in an aqueous environment, do have appreciable bactericidal properties. Bactericidal properties have been shown against *Staph. aureus*, *Staph. epidermidis*, and various streptococci, commonly found in and on the skin. While not being bound by a specific mechanism of action, it is believed that this action is a result of the greatly increased bioactivity of the small particulates, which leads to a sharply increased pH of the surrounding aqueous environment. The combined properties of being both broadly bactericidal while at the same time maintaining tissue biocompatibility make small particles of bioactive glass a suitable antibacterial treatment, in particular, for skin disorders such as dermal ulcers.

The bactericidal action increases with decreasing particle size. The preferred particle size depends, in part, on the initial bacterial burden and the desired bacterial kill. For normal bacterial loads and uninfected wounds, for example, a composition in the less than 20 micron size range is sufficient. However, for higher bacterial loads where the danger of infection appears pressing, the composition should include particles with a size less than five microns as measured by SEM or laser light scattering techniques.

An "effective, antibacterial amount of bioactive glass" refers to an amount of bioactive glass, with an appropriate particle size, which is effective at reducing the bacterial infection. Those of skill in the art can readily estimate the bacterial load in a wound, and use this estimate to determine an appropriate particle size and amount of bioactive glass to administer to the wound. As used herein, the term "antibacterial" is also used to refer to the ability of the compositions to reduce infections due to fungi and mold.

The present invention will be more clearly understood with reference to the following non-limiting examples.

EXAMPLES

Example 1
Treatment of a Wound with a Particulate Bioactive Glass in a Carrier A photograph was taken of a wound in patient with vasculitis taken soon after the wound was inflicted. This type of wound would typically require an overall healing time of about 3 months. The wound was treated with a mixture of particulate non-interlinked bioactive glass with a fine particle size, a topical antibiotic including sulfadiazine, and a petrolatum base carrier.

A second photograph was taken of the same wound, after treatment with the bioactive glass composition, 4 days after the first photograph. A third photograph of the same wound was taken 7 days after the second photograph. A fourth photograph of the same wound was taken 14 days after the second photograph. These photographs demonstrate that the wound is healing well. A similar wound on a patient with vasculitis would not be expected to show a similar degree of healing for at least about three months, if at all.

For example, the second photograph showed that, after only 4 days, seepage of the wound was stopped and the surface of the wound appeared dry. If one were to apply only a topical antibiotic to such a wound in a patient with vasculitis, it would normally take about 2 weeks to stop seepage. The third photograph showed that the healing mechanism was well underway and that fatty tissue had covered the surface of the wound after only 11 days. The fourth photograph showed that after only 18 days, the wound was about 50% healed. In a patient with vasculitis, it normally takes about 6–8 weeks to reach the 50% healed stage in a wound of the type pictured in the photographs.

Example 2
Treatment of Delayed Healing in a Diabetic Patient

A diabetic suffering from delayed healing lesions was treated with a mixture of particulate bioactive glass with a particle size less than 40 $\mu$m and an equal volume of NEOSPORIN™ antibiotic ointment. This ointment was substantially a mixture of antibiotic agents in a petrolatum base. The mixture was applied directly to the delayed healing lesions of about ½ cm by ½ cm. These lesions normally remain non-healing for over 14 days. The mixture was applied twice a day. Within 24 hours seepage ceased. Wound closure and healing was complete within 5 days. Within 48 hours, scar tissue was apparent around the edges of the defect.

As the scar tissue continued to develop, its appearance was much more like that of the surrounding tissue than is typical for an injury of the type being treated in this patient. After full development, the appearance of the scar tissue closely approximated that of the surrounding tissue.

Example 3
Anti-Bacterial Properties of Bioactive Glass

Small particulate bioactive glasses and highly porous bioactive glass possess anti-bacterial activity. In aqueous solutions, bioactive glass with a composition of 45% silicon dioxide, 24.5% sodium oxide, 24.5% calcium oxide and 6% phosphorous oxide causes a pH rise in aqueous solutions. The following experiment was carried out to demonstrate the anti-bacterial properties of the resulting solution.

Nutrient broth (10 ml) was added to 5 grams of particulate bioactive glass with a pore size between 355 and 500 $\mu$m, 5 grams of glass beads (not bioactive glass) with a particle size between 455 and 600 $\mu$m, and no glass beads. The resulting solutions were incubated with rotation for 1 h at 37 C. 950 $\mu$l of each supernatant was removed and added to 50 $\mu$l of an overnight culture of *S. sanguis*, and incubated for 1 h at 37 C. Survivors were enumerated by viable counting. A mean reduction in viable counts of 97% with the bioactive glass supernates was observed, with little or no kill with the glass bead supernates (13%).

To determine the contribution made by the pH change, the experiments were repeated with 50 $\mu$l of *S. Sanguis* added to unmodified BGS (bioactive glass solution), BGS and HCl (pH around 7.2), BGS and NaCl (pH around 9.8) (a control for chloride ion addition) and nutrient broth (pH around 7.2). Cultures incubated in high pH solutions showed reductions of viability of 81% (unmodified BGS) and 82% (BGS and NaCl), compared to 5% in the HCL treated BGS. Subsequent experiments with non-bioactive glass derived alkaline solutions (NaOH, pH 9.8) showed less antibacterial activity, with kills of 40%. This demonstrates that while decreasing the pH of bioactive glass supernates reduces their antibacterial activity, not all of the observed kills can be attributed to their high pH.

Example 4
Antiinflammatory Effects of Bioactive Glass Particles

A 1 ml suspension including 25 mg of bioactive glass in a 1:1 solution of fetal bovine serum and phosphate buffered saline was injected intraperitoneally into a group of five adult male mice, an additional group of five mice received the same solution without the bioactive glass to serve as a control. At two hours post-injection, the washed peritoneal fluid was examined for leukocyte recruitment and inflammatory mediators TNF-α and IL-1. Upon microscopic examination it was found that no additional cells above control levels were recruited. ELISA assays showed that TNF-α and IL-1 were not elevated above control levels. There was a modest increase in IL-6 levels, but in the absence of observable levels of TNF-α and IL-1, this indicates a general anti-inflammatory action. Given the physical presence of particulate matter that would otherwise induce a strong inflammatory response in this setting, the lack of recruited cells and their inflammatory signals represents a direct suppression of an inflammatory response.

Example 5
Anti-inflammatory Effects of Bioactive Glass Particles

An adult middle aged male was suffering from two open dermal lesions on the right forearm. These wounds were non-healing and highly inflamed, with large amounts of exudate, edema and erythema resulting from a local inflammatory response to the open, colonized wound. After two topical treatments with small particulate bioactive glass, all signs of local inflammation ceased, and the lesions proceeded to heal normally.

What is claimed is:

1. A wound or burn dressing comprising a bandage, a topical antibiotic and non-linked particles of bioactive glass wherein the bandage is cotton, gauze, fiberglass, or synthetic material and wherein the fiberglass is made from bioactive glass.

2. A wound or burn treatment applicator apparatus comprising a topical carrier in a first chamber, non-linked particles of bioactive glass in a second chamber and a mixing means for mixing the topical carrier and the bioactive glass.

3. The apparatus of claim 2, wherein the wound or burn treatment apparatus is a multi chamber syringe.

4. A method for improving the appearance of the scar formed during the healing of wounds or burns comprising contacting a wound or burn with an effective scar appearance improving amount of a non-linked, particulate bioactive glass.

5. The method of claim 4 wherein the bioactive glass is present in a composition comprising the bioactive glass in the form of non-linked, small particles of bioactive glass and a suitable carrier.

6. A method of reducing the level of inflammation in a wound by contacting the wound with an effective inflammation reducing amount of a bioactive glass, wherein the inflammation is chronic inflammation.

7. A method of reducing the level of bacterial infection in a wound comprising contacting the wound with an effective antibacterial amount of a bioactive glass, wherein the bioactive glass has a composition by weight percentage:

| Component | Percent |
|---|---|
| $SiO_2$ | 40–86 |
| CaO | 10–46 |
| $Na_2O$ | 0–35 |
| $P_2O_5$ | 2–8 |
| $CaF_2$ | 0–25 |
| $B_2O_3$ | 0–10 |
| $K_2O$ | 0–8 |
| MgO | 0–5. |

8. The method of claim 7, wherein the bioactive glass has a composition by weight percentage:

| Component | Percent |
|---|---|
| $SiO_2$ | 45 |
| CaO | 24.5 |
| $Na_2O$ | 24.5 |
| $P_2O_5$ | 6. |

9. A method of reducing the level of bacterial infection in a wound comprising contacting the wound with an effective antibacterial amount of a bioactive glass, wherein the bioactive glass has a particle size range less than about 20 microns as measured by SEM or laser light scattering techniques.

10. The method of claim 9, wherein the bioactive glass has a particle size range less than about 2 microns as measured by SEM or laser light scattering techniques.

* * * * *